United States Patent
Luzzani et al.

(10) Patent No.: US 10,314,814 B2
(45) Date of Patent: Jun. 11, 2019

(54) COMPOSITION COMPRISING 7-HYDROXYMATAIRESINOL

(71) Applicant: LINNEA S.A., Riazzino (Locarno) (CH)

(72) Inventors: Marcello Luzzani, Lipomo (IT); Massimiliano Carreri, Minusio (CH)

(73) Assignee: LINNEA S.A., Riazzino (Locarno) (CH)

( * ) Notice: Subject to any disclaimer, the term of this patent is extended or adjusted under 35 U.S.C. 154(b) by 0 days.

(21) Appl. No.: 15/308,272

(22) PCT Filed: May 13, 2015

(86) PCT No.: PCT/EP2015/060677
§ 371 (c)(1),
(2) Date: Nov. 1, 2016

(87) PCT Pub. No.: WO2015/173345
PCT Pub. Date: Nov. 19, 2015

(65) Prior Publication Data
US 2017/0056370 A1    Mar. 2, 2017

(30) Foreign Application Priority Data
May 15, 2014  (IT) .............................. MI2014A0892

(51) Int. Cl.
*A61K 45/06*   (2006.01)
*A61K 31/365*  (2006.01)

(52) U.S. Cl.
CPC ............ *A61K 31/365* (2013.01); *A61K 45/06* (2013.01)

(58) Field of Classification Search
CPC ... A61K 31/365; A61K 45/06; A61K 2300/00
See application file for complete search history.

(56) References Cited

U.S. PATENT DOCUMENTS 6,451,849 B1   9/2002 Ahotupa et al.
9,669,006 B2 * 6/2017 Minatelli ............. A61K 31/365

2003/0100514 A1   5/2003 Ahotupa et al.
2008/0057140 A1 * 3/2008 Unkila ................... A61K 31/05
                                                    424/725
2017/0165308 A1 * 6/2017 Ahlnas ................. A61K 36/15

FOREIGN PATENT DOCUMENTS

WO      00/59946 A1   10/2000
WO   2006/072647 A1   7/2006

OTHER PUBLICATIONS

Lina et al. (Regulatory toxicology and Pharmacology 41(2005) 28-38.*
Health (2009).*
Chedraui et al. (Gynecological Endocrinology, 2011; 27(9): 685-691).*
Cosentino et al. (International Immunopharmacology 10 (2010) 339-343).*
Krause et al. (The Journal of Lipid Research, 25, 97-110, 1984).*
Giorgio Biasiotto, et al., "Oilseeds ameliorate metabolic parameters in male mice, while contained lignans inhibit 3T3-L1 adipocyte differentiation in vitro," European Journal of Nutrition, DOI 10.1007/s00394-014-0675-2, Feb. 2014, 15 pages.
Marc-Andre Cornier, et al., "The Metabolic Syndrome," Endocrine Reviews, vol. 29, No. 7, Dec. 2008, pp. 777-822.
M. Penza, et al., "Genistein Affects Adipose Tissue Deposition in a Dose-Dependent and Gender-Specific Manner," Endocrinology, vol. 147, No. 12, Dec. 2006, pp. 5740-5751.
An-Sheng Zhang, et al., "Red Cells, Iron, and Erythropoiesis: Suppression of hepatic hepcidin expression in response to acute iron deprivation is associated with an increase of matriptase-2 protein," Blood, vol. 117, No. 5, Feb. 3, 2011, 24 pages.
Eliana Spilioti, et al., "Lignans 7-hydroxymatairesinol and 7-hydroxymatairesinol 2 exhibit anti-inflammatory activity in human aortic endothelial cells," Mol. Nutr. Food Res. 2014, vol. 58, pp. 749-759.
Marco Cosentino, et al., "Immunomodulatory activity of the lignan 7-hydroxymatairesinol potassium acetate (HMR/lignan™) extracted from the heartwood of Norway spruce (*Picea abies*)," International Immunopharmacology, vol. 10, 2010, pp. 339-343.
International Search Report dated Jul. 3, 2015 in PCT/EP2015/060677 filed May 13, 2015.

* cited by examiner

*Primary Examiner* — Shirley V Gembeh
(74) *Attorney, Agent, or Firm* — Oblon, McClelland, Maier & Neustadt, L.L.P.

(57) ABSTRACT

A composition comprising 7-hydroxymatairesinol (HMR), or a stereoisomer, salt, complex, adduct or derivative thereof, or an extract containing them for preventing, alleviating or ameliorating the metabolic syndrome conditions.

16 Claims, 9 Drawing Sheets

\* $p \leq 0.05$ ; \*\* $p < 0.01$ ; \*\*\* $p < 0.001$

* $p \leq 0.05$

* $p \leq 0.05$ ; ** $p < 0.01$

* $p \leq 0.05$

COMPOSITION COMPRISING 7-HYDROXYMATAIRESINOL

FIELD OF THE INVENTION

The present invention relates to a composition comprising 7-hydroxymatairesinol for ameliorating the metabolic syndrome conditions. In particular, the present invention relates to a pharmaceutical composition and/or a food product able to able to preventing, alleviating or treating the metabolic syndrome, such a composition comprising 7-hydroxymatairesinol, or a stereoisomer, salt, complex, adduct or derivative thereof, or an extract containing them.

BACKGROUND OF THE INVENTION

The metabolic syndrome (MetS) is a co-occurrence of several medical conditions. The high prevalence of MetS, visceral obesity (i.e. excessive fat accumulation in the abdomen) with associated high blood pressure, dyslipidemia and high blood glucose, is a major threat to people health, being associated with a substantial decrease in health-related quality of life.

According to WHO (World Health Organization), OECD (Organization for Economic Cooperation and Development) and the WHF (World Heart Federation), 30-80% of the adult population in the European Region is overweight (has a body mass index (BMI) over 25). The average BMI for the European population is nearly 26.5 and obesity (BMI over 30) affects up to a third of its adult population. This means that about 130 million of the 400 million European adults are overweight or obese. Moreover, childhood obesity is an acute health crisis. About 20% of children are overweight, and a third of these are obese.

MetS is a complex of lifestyle based diseases that consists of several correlated risks of metabolic origin. In addition to dyslipidemia, hypertension and hyperglycemia, the syndrome carries a proinflammatory state. Subjects affected by the MetS are at increased risk for cardiovascular disease (2-fold), type 2 diabetes (5-fold), respiratory failure, gallbladder disease, certain types of cancer and psychosocial problems.

MetS is a diet-related disease and it is believed that MetS could be prevented by applying a correct lifestyle and diet.

Although it is generally agreed that first-line clinical intervention for the metabolic syndrome is a lifestyle change, this is insufficient to normalize the risk factors in many patients, and so residual risk could be high enough to justify drug therapy.

However, at present there are no approved drugs that can reliably reduce all the metabolic risk factors over the long term, and so there is growing interest in therapeutic strategies that might target multiple risk factors more effectively, thereby minimizing problems with multiple assumption of drugs for prolonged periods of time.

Lignans are a group of compounds found in fiber-rich foods such as cereals, oilseed, nuts, vegetables (*brassica*) and fruits (berries), typically regarded as components of healthy diets.

They are expected to have beneficial effects in humans after fermentative conversion in the colon, producing enterolactone and enterodiol, favorably influencing metabolic parameters related to the MetS. Subpopulations with higher consumption of lignans display considerable lower disease frequency.

A few randomized controlled studies have shown beneficial effects of diets supplemented with lignan-rich seeds (oilseeds) in the control of metabolic diseases such as dyslipidemia and type 2 diabetes. Studies have also been conducted in animal models, in which partially purified lignan fractions improved blood lipids, enhanced glycemic control and improved type 1 and type 2 diabetes.

A few in-vitro studies have also been performed to identify the lignans as antioxidants, phytoestrogens and modulators of nuclear receptors.

A recent study (Biasotto G. et al., "*Oilseeds ameliorate metabolic parameters in male mice, while contained lignans inhibit 3T3-L1 adipocyte differentiation in vitro*", European Journal of Nutrition, 2014) illustrated the amelioration of metabolic parameters in male mice fed with high quantity of whole sesame and flaxseeds (20% w/w in the food), two of the most lignan-rich food sources, containing about 1% by weight of total lignans. Sesame extracts mainly comprise sesamin (SES) and pinoresinol (PIN) lignans, while flaxseeds extracts mainly comprise secoisolariciresinol (SEC) lignan. 7-hydroxymatairesinol (HMR) is only present in minor amount in sesame extracts and is not present at all in flaxseeds extracts.

HMR is the main single component of lignans in Norway spruce (*Picea abies*), reaching a concentration of about 60 percent of total lignans, which occurs mainly in unconjugated free form.

Lignan concentration in thick roots is 2-3 percent. Abundance of lignans occur in the heartwood of branches (5-10 percent) and twists, especially in the knots, where the amount of lignans may be higher than 10 percent. These concentrations are about hundred-fold compared to ground flaxseeds powder known as lignan-rich material.

WO00/59946 and U.S. Pat. No. 6,451,849 disclose the use of HMR for prevention of cancers, certain non-cancer, hormone dependent diseases and/or cardiovascular diseases.

WO2006/072647 discloses the use of HMR for preventing or alleviating of symptoms relating to estrogen deficiency in an individual, such as menopausal or postmenopausal symptoms, climacteric symptoms, hot flushes, vaginal dryness, vaginal atrophy, atrophy of the lower urinary tract, loss of bone mineral content, menopausal vasomotor symptoms, mood swings, insomnia, osteoporosis or any other menopause associated condition.

SUMMARY OF THE INVENTION

The Applicant faced the problem of selecting an active compound able to preventing, alleviating or treating the co-occurrence of the medical conditions associated with metabolic syndrome.

In particular, the Applicant faced the problem of selecting an active compound able to preventing, alleviating or treating visceral obesity associated with one or more of high blood pressure, dyslipidemia (i.e., increased triglycerides and reduced HDL-C) and high blood glucose.

The Applicant surprisingly found that HMR was able to reduce obesity, dyslipidemia, and glycaemia.

The Applicant also surprisingly found that HMR was able to reduce the number and area of adipocytes as well as to reduce the concentration of pro-inflammatory cytokines in the epidydimal adipose tissue and liver.

Further, the Applicant surprisingly found that HMR was able to contribute to the regulation of genes of the lipid metabolism in the liver (such as the PPARg gene and TFEB gene) and in the epidydimal adipose tissue (such as the ATGL mRNA, PLA2g7 gene, and LPL gene).

Finally, the Applicant unexpectedly found that HMR was also able to reduce the cellular oxidative stress and to regulate the iron metabolism, even related to the metabolic syndrome.

Accordingly, a first aspect of the present invention relates to the use of 7-hydroxymatairesinol (HMR) for preventing, alleviating or treating the metabolic syndrome conditions.

More in particular, the present invention relates to the use of HMR for preventing, alleviating or treating the co-occurrence of the medical conditions associated with metabolic syndrome, such as visceral obesity, steatosis, inflammation, dyslipidemia (i.e., increased triglycerides and reduced HDL-C), insulin sensitivity and high blood glucose.

A second aspect of the present invention relates to a composition, such as a pharmaceutical composition or a food product, comprising 7-hydroxymatairesinol (HMR), together with one or more additional ingredient and/or excipient for preventing, alleviating or treating the metabolic syndrome conditions.

A third aspect of the present invention relates to a method for preventing, alleviating or treating the metabolic syndrome conditions in a person in need thereof comprising administering to said person an effective amount of 7-hydroxymatairesinol (HMR).

For the purposes of the present description and the claims which follow, the term "7-hydroxymatairesinol" is intended to include a stereoisomer, salt, complex, adduct, or derivative thereof, or an extract which contains them.

In the context of the present invention, the term "derivative of the 7-hydroxymatairesinol" refers to compounds comprising modifications that occur naturally in wood or which are generated during the extraction from the timber. The natural modifications of 7-hydroxymatairesinol are for example the formation of glycosides and aglycones of 7-hydroxymatairesinol. The most important derivatives of 7-hydroxymatairesinol that are obtained during the extraction of wood are dimethylmatairesinol, 7-methoxymatairesinol, 7-oxomatairesinol, didemethylmatairesinol, isohydroxymatairesinol, enterolactone, conidendrin, and 7',8'-dehydro-7-hydroxymatairesinol.

DETAILED DESCRIPTION OF THE INVENTION

This invention relates to the use of 7-hydroxymatairesinol (HMR) for preventing, alleviating or treating the metabolic syndrome conditions.

The chemical structure of HMR is represented by the following formula (I).

HMR is a lignan, i.e., a group of chemical compounds found in plants derived from phenylalanine via dimerization of substituted cinnamic alcohols, known as monolignols, to a dibenzylbutane skeleton. Lignans are one of the major classes of phytoestrogens, which are estrogen-like chemicals and also act as antioxidants.

Flax seeds and sesame seeds contain higher levels of lignans than most other foods. Considerable amounts of lignans are also found in coniferous trees. The type of lignans differs in different species and the amounts of lignans vary in different parts of the trees.

HMR is the far most abundant single component of lignans in spruce (*Picea abies*) extracts, wherein reaches a concentration of about 60% w/w of total lignans.

In spruce, lignan concentration in thick roots is 2-3 percent. Abundance of lignans occur in the heart wood of branches (5-10 percent) and twists, especially in the knots, where the amount of lignans may be higher than 10 percent. These concentrations are about hundred-fold compared to ground flaxseeds powder known as lignan-rich material.

Isolation of HMR for use in this invention can be made from oversize chip fraction (containing branches, twists and knots) of compression wood of spruce (*Picea abies*). Total extract of *Picea abies* (TEP, containing HMR and the isomer) and HMRlignan™ purified HMR (containing mainly HMR) are commercially available from Linnea S A, Riazzino, Switzerland.

The term "metabolic syndrome" (MetS) refers to a clustering of components that reflects overnutrition, sedentary lifestyles, and resultant excess adiposity, and relates to a co-occurrence of medical conditions such as visceral obesity, steatosis, inflammation, dyslipidemia (i.e., increased triglycerides and reduced HDL-C), insulin sensitivity and high blood glucose. For example, the metabolic syndrome includes disorders based on diagnostic standards such as (i) obesity, (ii) blood pressure, (iii) glucose, (iv), triglycerides, and (v) cholesterol.

In particular, the most recent definition of metabolic syndrome has been provided by the IDF (International Diabetes Federation) in the publication "The IDF consensus worldwide definition of the metabolic syndrome" (2006) and in the article by P. Zimmet and G. Alberti, "The IDF definition: why we need a global consensus", Diabetes Voice, May 2006, Volume 51, Special Issue, Pages 11-14.

By the term "metabolic syndrome" means the occurrence of a condition of general obesity, characterized by the presence of an abdominal circumference equal to or greater than 94 cm in men and equal to or greater than 80 in the woman or a body mass index greater than 30 kg/m2, together with the presence of at least two of the following conditions: (i) systolic blood pressure equal to or greater than 130 mmHg, or diastolic blood pressure equal to or higher than 85 mmHg; (ii) glucose equal to or greater than 100 mg/dL; (iii) blood triglycerides greater than 150 mg/dL; and (iv) HDL cholesterol less than 40 mg/dL in men and 50 mg/dL in women.

In addition, cases corresponding to any one of the conditions above are defined as belonging to the potential metabolic syndrome group, and conditions in the potential metabolic syndrome group are also included in metabolic syndrome. Anyway, other conditions on other voluntary diagnostic standards are also not excluded. For example, a review of metabolic syndrome definitions and conditions can be found in M. A. Cornier et al., The Metabolic Syndrome, Endocrine Reviews, December 2008, 29(7):777-822.

Metabolic syndrome preventing, alleviating or treating refers to prevention, alleviation or treatment of conditions for metabolic syndrome patients and for any condition diagnosed as the potential metabolic syndrome group.

For example, reduced white adipose tissue, blood glucose values, blood insulin concentrations, blood cholesterol, blood LDL cholesterol, and blood triglyceride concentrations, are included.

In addition, metabolic syndrome prevention, alleviation or treatment comprises reducing liver steatosis, improving the glucose tolerance, reducing insulin resistance, reducing the inflammatory cytokines like IL-6 and TNF-alfa, regulating the expression of genes of the lipid metabolism like ATGL mRNA, PLA2g7, LPL, PPARg and TFEB, reducing the cellular oxidative stress.

This invention also relates to a composition, such as a pharmaceutical composition or a food product, comprising HMR, together with one or more additional ingredient and/or excipient for preventing, alleviating or treating the metabolic syndrome conditions. Advantageously, the additional ingredient and/or excipient is an antioxidant.

The pharmaceutical composition according to this invention is preferably an oral formulation. The required amount of the active compound (HMR) will vary with the particular condition to be prevented. A typical dose of HMR ranges from about 10 to about 500 mg per day and adult person, preferably from about 30 to about 300 mg per day and adult person.

The form of the composition of the present invention may be represented by a form which is useful for the oral administration, such as for example solution, suspension, syrup, tablets, granules, pellets, capsules, lozenges and pills.

The food product according to this invention can be any edible, non-toxic solid or liquid product suitable to be admixed with HMR without affecting the properties of HMR. The role of the product is mainly to make the exact dosage of HMR easier.

The food product according to this invention is especially a functional food, a nutritional supplement, a nutraceutical, a health food, or any food product. The concentration of HMR in the food product will be properly calculated, depending on the type of food product, in order to ensure a supply of HMR between about 10 and about 500 mg per day for adult, preferably between about 30 and about 300 mg per day per adult.

The functional food according to this invention can, for example be in the form of butter, margarin, biscuits, bread, cake, candy, confectionery, yogurt or another fermented milk product, or cereal such as muesli.

The additional ingredient and/or excipient of the pharmaceutical composition of the present invention can be any pharmaceutically acceptable ingredient and/or excipient The term pharmaceutically acceptable excipient is understood to comprise without any particular limitations any material which is suitable for the preparation of a pharmaceutical composition which is to be administered to a living being. As already discussed, depending upon the role performed, excipients are classified into (i) filler excipients, (ii) production excipients, (iii) preservative excipients, and (iv) presentation excipients. These materials, which are known in the art, are for example (i) diluents, absorbents, adsorbents, fillers and humectants, (ii) lubricants, binders, glidants, plasticisers and viscosity modifiers, (iii) preservatives, antimicrobials, antioxidants and chelating agents, and (iv) flavourings, sweeteners and colouring agents.

The additional ingredient and/or excipient of the food product of the present invention can be any edible ingredient and/or excipient.

Advantageously, the food product of the present invention comprises at least one edible ingredient selected from the group comprising carbohydrates, proteins, amino acids and derivatives, lipids, phospholipids, vitamins and mineral salts.

The food product of the present invention may be in the form of a complete foodstuff, a food supplement, a nutritional solution for gastro-enteric administration, for example for enteric feeding administered through a naso-gastric and naso-enteric tube, a nutritional solution for parenteral administration, or a foodstuff or supplement for diabetic individuals.

A complete foodstuff comprises all the nutritional substances necessary to satisfy the user's daily requirements in terms of the intake of substances and energy. Thus the formulation must contain carbohydrates, in a quantity of between 30% and 70% by weight, proteins in a quantity between 10% and 30% by weight and lipids between 20% and 40% by weight.

In addition to this the formulation must be capable of providing between 2000 and 2900 kcal per day, and may be in the form of a solid, for dissolution or dispersion in water or other beverage, or a liquid, in a form which is ready for use or as a concentrate. Lesser or greater energy intake may be provided for particular situations (dietary or sporting regimens).

A food supplement can contain only some of the nutritional substances required to satisfy the user's daily requirements in terms of proteins and energy intake. Thus the formulation will be capable of providing less than 1500 kcal, preferably from 100 to 1000 kcal per day. Alternatively, the food supplement can be free of nutritional substances. In such a case, the food formulation does not provide energy intake and only comprises conventional excipients as described for pharmaceutical compositions. Again in this case the formulation may be in solid or liquid form as described above, for addition to normal diet or as a component of normal diet.

The food product of the present invention may contain further conventional food additives to improve its appearance, pleasantness and preservation, such as for example colouring agents, preservatives, antioxidants, acidity regulators, thickeners, stabilisers, emulsifiers, flavour enhancers, flavourings, humectants and sweeteners.

BRIEF DESCRIPTION OF THE DRAWINGS

The present invention will be better understood by reading the following examples, given by way of illustration and not of limitation, to be read with the accompanying drawings, wherein:

FIGS. 2(a, b and c) shows the average total fat mass, the average epidymal fat tissue mass, and the average gluteal fat tissue mass, respectively, for each mice group measured according to test 1.

EXAMPLES

A group of 140 mice (C57BL/6J) was divided in four sub-groups, group 1 having twenty mice and groups 2 to 4 having forty mice each. Group 1 was fed for 60 days with a low fat (LF) diet (providing 10% calories from fat). Group 2 was fed for 60 days with a high fat (HF) diet (providing 50% calories from fat). Groups 3 and 4 were fed for 60 days with a high fat diet and with 3 mg/kg/day of HMRlignan™ purified HMR (HF+HMR) or 10 mg/kg/day of a total extract of *Picea abies* (HF+TEP), respectively.

The composition of the LF and HF diet is reported in the following Table 1. LF and HF diets were commercially available from Piccioni Srl, Rome, Italy. HMRlignan™ purified HMR and TEP were commercially available from Linnea S A, Riazzino, Switzerland.

TABLE 1

| Ingredient | LF diet (% w/w) | HF diet (% w/w) |
| --- | --- | --- |
| Casein | 20.0 | 25.0 |
| L-Cystine | 0.3 | 0.3 |
| Corn Starch | 25.0 | 10.8 |
| Maltodextrin | 8.5 | 5.0 |
| Sucrose | 31.5 | 20.5 |
| Cellulose | 5.0 | 5.0 |
| Corn Oil | 2.5 | 2.5 |
| Lard | 2.0 | 13.0 |
| Mineral Mix | 4.0 | 4.0 |
| Vitamin Mix | 1.0 | 1.0 |
| Choline bitartrate | 0.2 | — |
| Choline chloride | — | 0.4 |
| Hydrogenated coconut oil | — | 12.5 |

Mice were kept in animal cabinets maintained at a temperature of 23° C., with natural light/dark cycles. Before treatments, mice were put 5 days on an low fat diet. Mice were fed by gavage daily for 60 days (groups 3 and 4), whilst control groups (1 and 2) received by gavage the carrier only (corn oil). The animals were sacrificed by cervical dislocation and the tissues dissected and immediately frozen on dry ice or fixed for histological evaluation.

The following tests were performed.

Test 1—Fat Mass and Lean Mass Quantification.

The measurement of fat mass and lean mass was performed by Echo Magnetic Resonance Imaging system (EchoMRI) (Medical System, Houston, Tex.).

EchoMRI provides the most precise measurements of whole body composition parameters (total body fat and lean mass), in alive mice without the need of anesthesia or sedation and in less than 1 minute. Alterations in mouse whole body composition were assessed as a result of exposure to modified diets. Measurements of fat and lean mass and body weight were made periodically for the whole period of the study.

The EchoMRI-100™ QNMR system was housed in a dedicated area to minimize the entry of disease or contaminants. Prior to each QNMR run, the system was calibrated using a standard provided by Echo Medical System. Each mouse was placed into an appropriate size tube and placed in the QNMR machine for measurements. The mouse was subjected to a predetermined sequence of radio frequency energy during a 47 seconds run. Three sequential independent scans were conducted for each mouse and the data was automatically transferred to the database. The output information was expressed as lean tissue mass and fat mass in grams.

Figure 1:
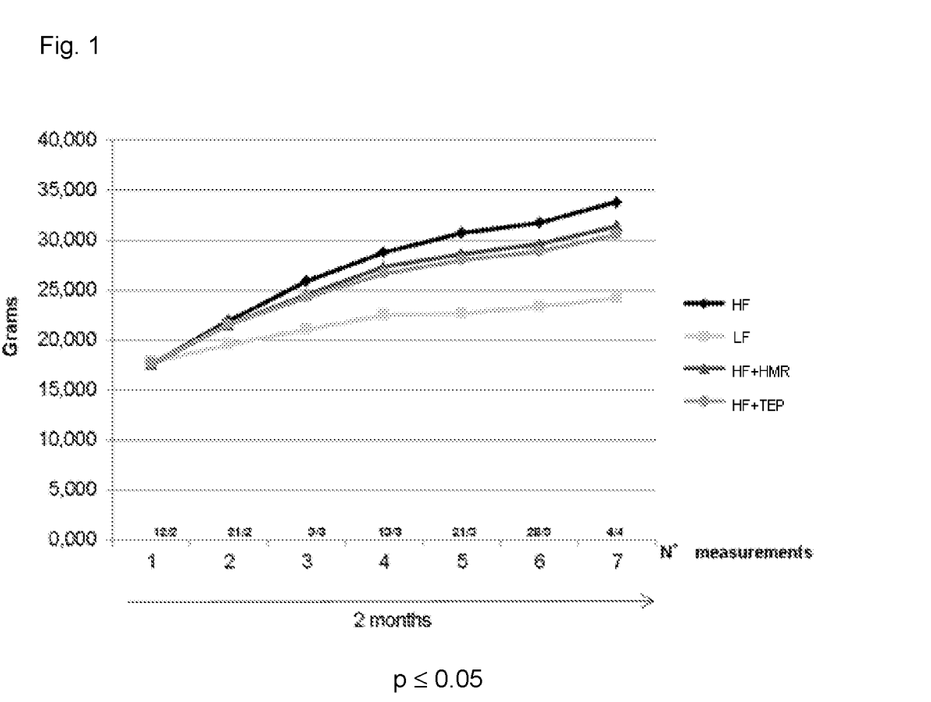
FIG. 1 shows the increase of the average whole body weight of for each mice group measured according to test 1.
Figure 2A:
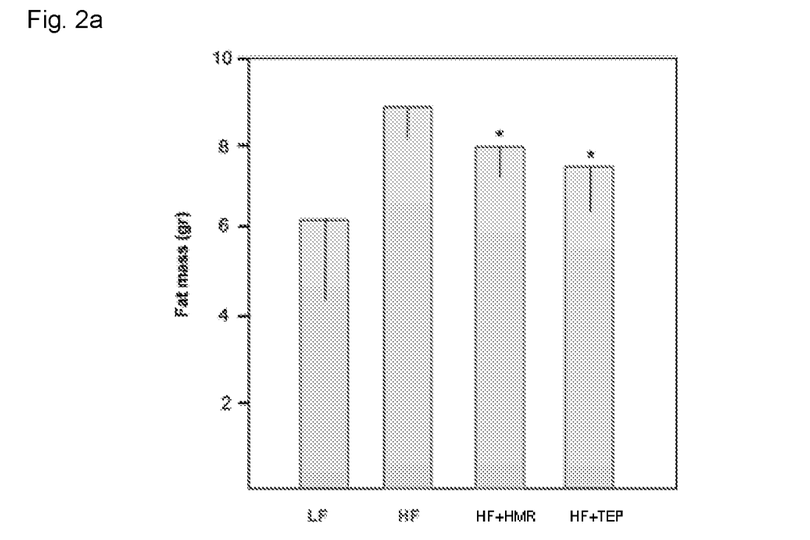
Figure 2B:
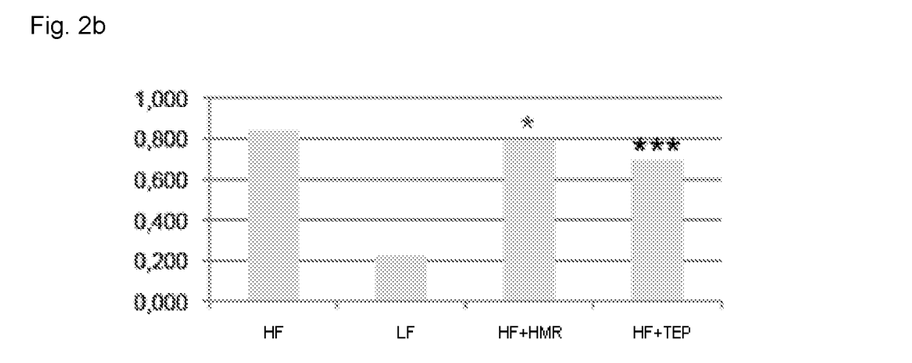
Figure 2C:
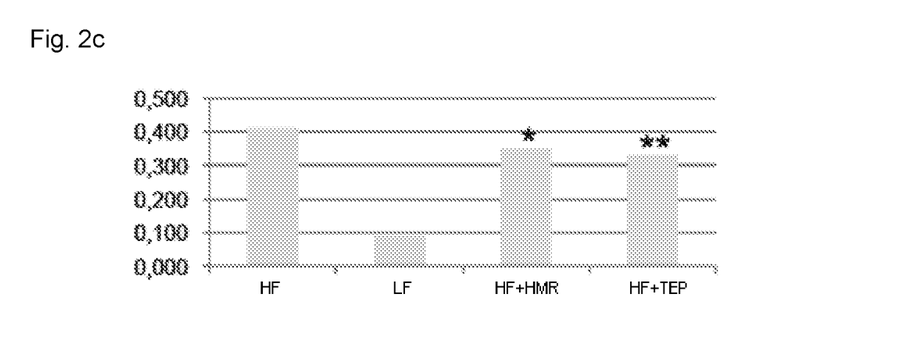

The increase of the average whole body weight for each group along the whole period of observation was plotted in FIG. 1. The average total fat mass, the average epidymal fat tissue mass, and the average gluteal fat tissue mass for each group at the end of the period of observation were reported in FIGS. 2a, 2b and 2c, respectively.

Test 2—Histological Examination

Fresh epidydimal adipose tissue was fixed in formaldehyde, embedded in paraffin and sliced into 3-µm sections. Sections were stained with hematoxylin, counterstained with eosin, then coverslipped with DPX (BDH, Poole, UK). Images acquisition was obtained by a digital camera (Nikon Digital Camera DMX 1200).

Average adipocyte area was calculated at ×20 magnification with a dedicated software (Image Pro Plus; Imaging and Computer, Milan). In all samples, at least four different fields of three different tissue sections have been evaluated.

The results are summarized in the following Table 2.

TABLE 2

| | Group 1 LF | Group 2 HF | Group 3 HF + HMR | Group 4 HF + TEP |
| --- | --- | --- | --- | --- |
| Average area (µm$^2$) | 9275 | 20832 | 18478 | 19628 |

Due to the very high variability of the shape and size of the cells and to the manual histological examination the data are only indicative. The data of group 2 vs group 1 and the data of group 3 vs group 2 are statistically different.

Test 3—Liver Steatosis

Fresh liver tissue was fixed in formaldehyde, embedded in paraffin and sliced into 3-µm sections. Sections were stained with hematoxylin, counterstained with eosin, then coverslipped with DPX (BDH, Poole, UK). Images acquisition was obtained by a digital camera (Nikon Digital Camera DMX 1200). A sample image of the four groups was illustrated in FIG. 3.

Figure 3:
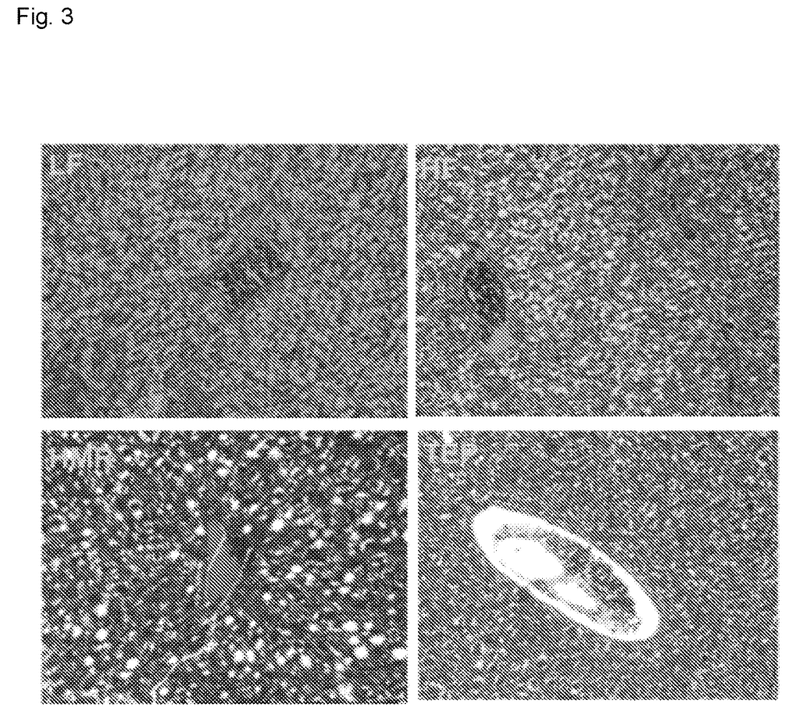
FIG. 3 shows a sample image of sections of liver tissue for each mice group according to test 3.

Livers from group 1 mice exhibited a normal hepatic structure, while livers from group 2 mice revealed micro- and macro vesicular steatosis. Livers from groups 3 and 4 showed some vacuoles, much less than group 2.

Test 4—Glucose Tolerance Tests

For glucose tolerance tests animals were fasted overnight for 12 hours and blood sample were obtained from the tail vein. Animals were then injected intraperitoneally with 2 g/Kg body weight of glucose, and blood samples were taken at the intervals indicated in FIG. 4. The glucose concentration was evaluated with standard method (Benjamin B. Whiddon and Richard D. Palmiter. *Ablation of Neurons Expressing Melanin-Concentrating Hormone (MCH) in Adult Mice Improves Glucose Tolerance Independent of MCH Signaling. J Neurosci.* 2013 Jan. 30; 33(5): 2009-2016).

Figure 4:
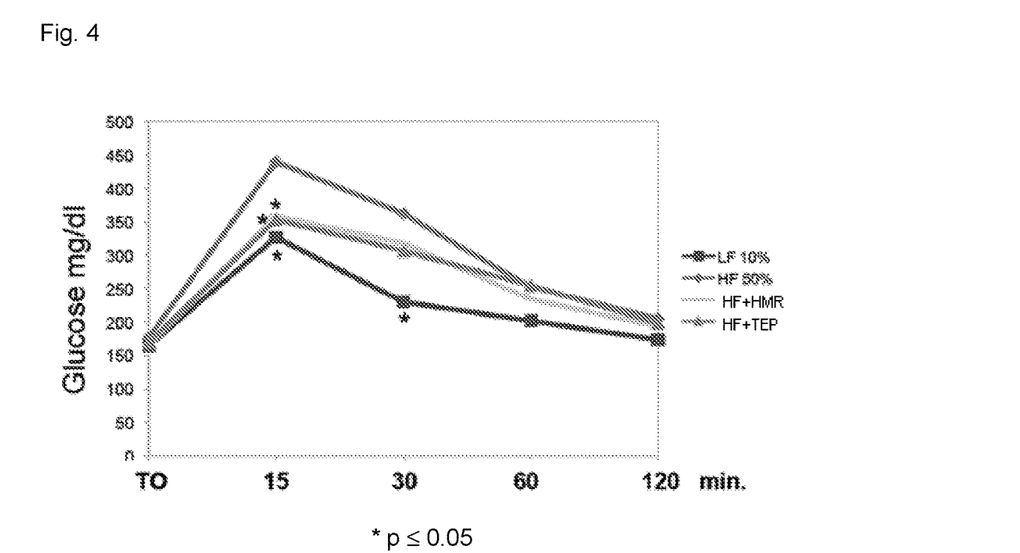
FIG. 4 shows the glucose concentration for each mice group measured according to test 4.

The results were illustrated in FIG. 4.

Test 5—Determination of Homeostasis Model Assessment of Insulin Resistance

The homeostatic model assessment of insulin resistance (HOMA-IR) was calculated using glucose and insulin concentrations obtained after 6 hours of food withdrawal, using the HOMA Calculator (Diabetes Trials Unit), the Oxford Centre for Diabetes, Endocrinology and Metabolism: homa.calculator@dtu.ox.ac.uk. Plasma insulin levels were measured with an insulin ELISA kit (Millipore, Mouse Insulin 96 well plate assay; CAT. N° EZRMI-13K).

Figure 5:
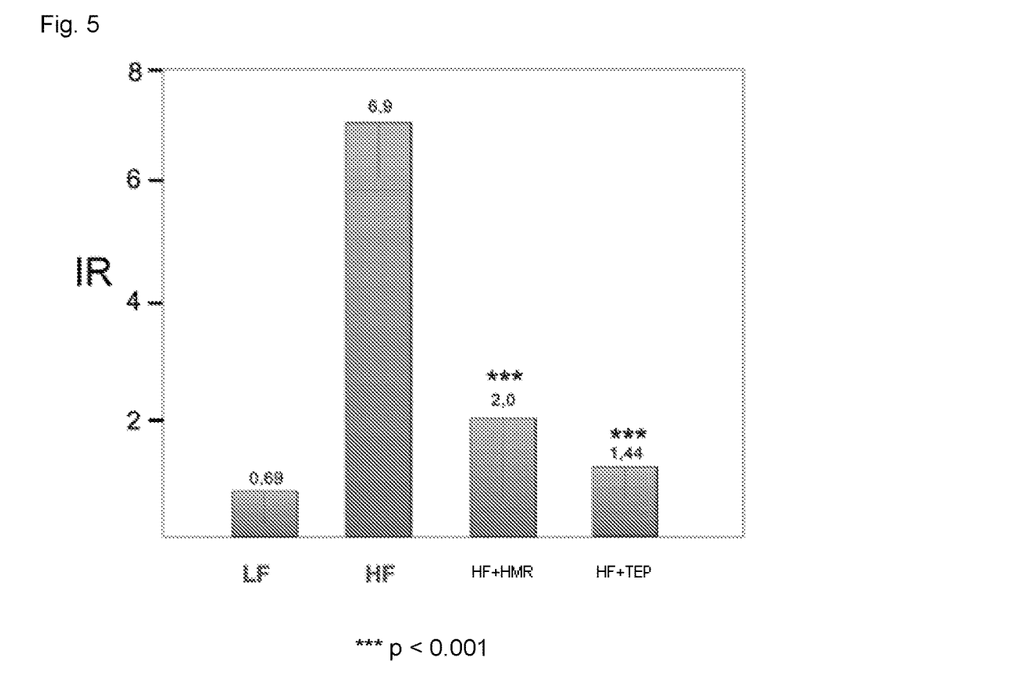
FIG. 5 shows the IR values for each mice group measured according to test 5.

The results are summarized in the following Table 3 and in FIG. 5.

TABLE 3

|  | % B | % S | IR |
|---|---|---|---|
| Group 1 | 64.4 | 121.0 | 0.69 |
| Group 2 | 101.0 | 15.0 | 6.97 |
| Group 3 | 55.0 | 31.9 | 2.04 |
| Group 4 | 35.0 | 104.0 | 1.44 |

% B: Steady state beta cell function
% S: Insulin sensitivity
IR: Insulin resistance Test 6—Lipid Profiles The concentration in blood of cholesterol (Total), cholesterol HDL (HDL), cholesterol LDL (LDL) and triglycerides (TG) were determined according to standard methods, by using an ILab ARIES analyzer (Instrumentation Laboratory Company, Lexington, Mass., USA) and dedicated reagents kits IL Test (Instrumentation Laboratory Company, Lexington, Mass., USA)

Reagents:
IL Test HDL Cholesterol: Code 0018255740
IL Test LDL Cholesterol: Code 0018256040
IL Test Triglyceride: Code 0018255640
IL Test Cholesterol: Code 0018250540

The results are summarized in the following Table 4.

TABLE 4

|  | Total | HDL | LDL | TG |
|---|---|---|---|---|
| Group 1 | 114 | 79 | 18 | 88 |
| Group 2 | 220 | 133 | 56 | 153 |
| Group 3 | 209 | 129 | 51 | 140 |
| Group 4 | 196 | 124 | 43 | 130 |

Test 7—Inflammatory Cytokines

The expression of inflammatory cytokine mRNA was measured in the epidydimal adipose tissue (IL-6 and TNF-alfa) and liver (IL-6) in the four groups of mice according to standard procedures as follows.

Total RNA was extracted from 10 to 30 mg of tissue using the RNeasy Lipid Tissue Kit (Qiagen, Maryland, USA) and following the manufacture's instruction. RNA for each sample was reversed transcribed using high capacity cDNA Archive Kit (Applied Biosystems, Foster City, Calif.). Quantitative PCR was performed using Assay on Demand kits based on TaqMan chemistry (Applied Biosystems). RT-PCR reactions were performed on an ABI PRISM 7000 Sequence Detection System instrument and data analysis was done with the ABI PRISM 7000 SDS software (Applied Biosystems). 18S RNA was used as the reference housekeeping gene. Specific oligonucleotides pairs were designed by the Applied Biosystems service. Calculations were done as described for the Comparative Method in the User Bulletin 2 of ABI PRISM sequence detection system. A detailed description of the above method can be found in "Biasotto G. et al., "Oilseeds ameliorate metabolic parameters in male mice, while contained lignans inhibit 3T3-L1 adipocyte differentiation in vitro", European Journal of Nutrition, 2014".

Figure 6A:
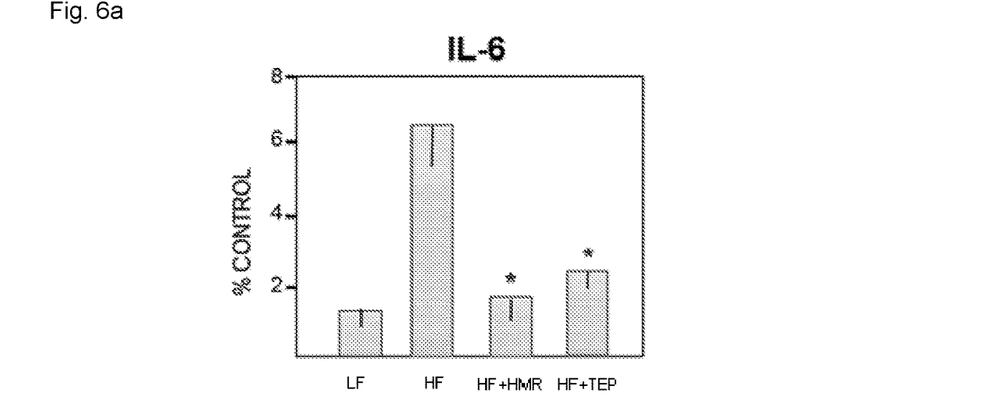
FIGS. 6a, 6b and 6c show the expression of inflammatory cytokine mRNA in the epidydimal adipose tissue (IL-6—FIG. 6a—, and TNF-alfa—FIG. 6b) and liver (IL-6—FIG. 6c) for each mice group measured according to test 7
Figure 6B:
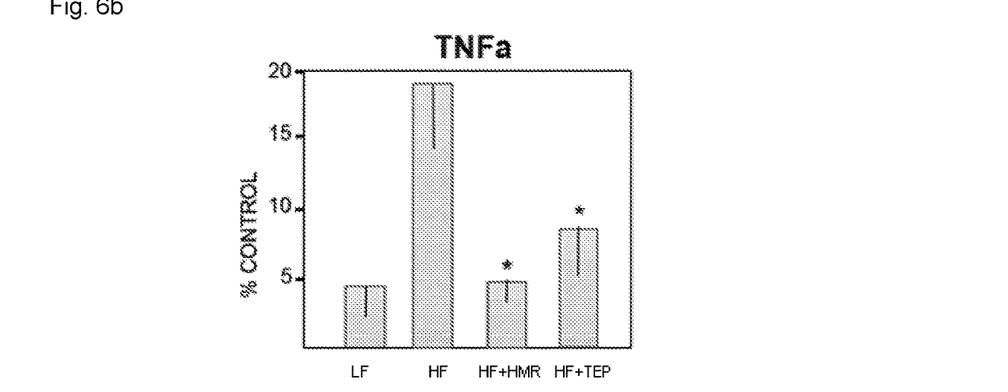
Figure 6C:
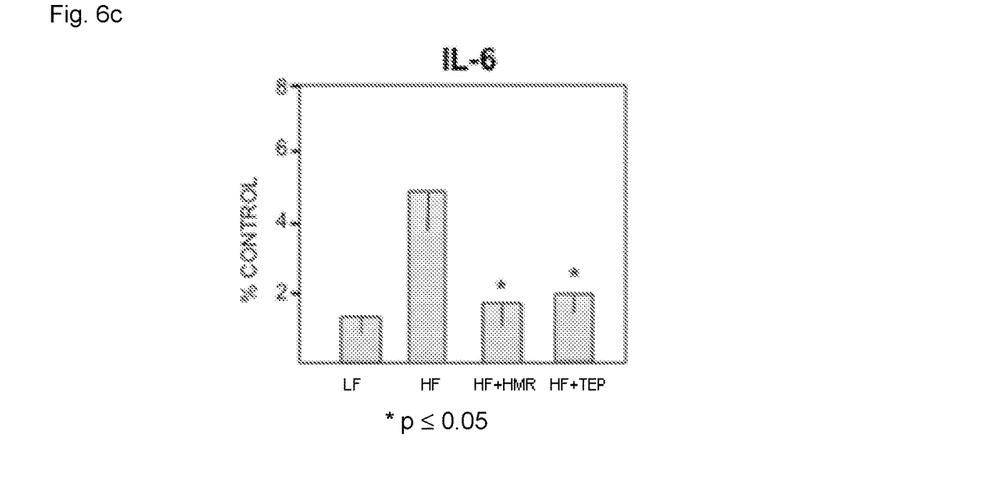

The results were illustrated in FIGS. 6a, 6b and 6c.

Test 8—Regulation of Genes of the Lipid Metabolism (Epidydimal Adipose Tissue)

Obesity is associated with increased triacylglycerol (TAG) storage in adipose tissue and insulin resistance. ATGL mRNA is decreased in adipose tissue of insulin resistant human subjects. The degree of IR and hyperinsulinemia in obesity rather than the increase in fat mass and body fat distribution per se is associated with a reduced ATGL mRNA.

PLA2g7 is the gene encoding PAF-AH (platelet activating factor acetylhydrolase), an adipose and circulating enzyme likely to play a role in obesity-related inflammation. In addition to having an anti-inflammatory activity by degrading PAF, PAF-AH may also exert proinflammatory activity by massively hydrolyzing phospholipids to generate lysophosphatidylcholine (lys-PC) and free oxidized fatty acids, both pro-inflammatory mediators responsible for the proatherogenic activity of oxidized LDL. Upregulation of these genes in adipocytes may also result in changes in the extracellular matrix (tissue remodeling) to accommodate adipose tissue expansion.

Lipoprotein lipase (LPL) is a member of the lipase gene family, which includes pancreatic lipase, hepatic lipase and endothelial lipase. LPL hydrolyzes triglycerides in lipoproteins, such those found in chylomicrones and very low-density lipoproteins (VLDL), into free fatty acids and one monoacylglycerol molecule. It is also involved in promoting the cellular uptake of chylomicron remnants, cholesterol-rich lipoproteins and free fatty acids. LPL is mostly distributed in adipose, heart, and skeletal muscle tissue and mammary lactating gland The expression of ATGL, PLA2g7 and LPL mRNA was measured in the epidydimal adipose tissue of the four groups of mice according to standard procedures as follows.

Total RNA was extracted from 10 to 30 mg of tissue using the RNeasy Lipid Tissue Kit (Qiagen, Maryland, USA) and following the manufacture's instruction. RNA for each sample was reversed transcribed using high capacity cDNA Archive Kit (Applied Biosystems, Foster City, Calif.). Quantitative PCR was performed using Assay on Demand kits based on TaqMan chemistry (Applied Biosystems). RT-PCR reactions were performed on an ABI PRISM 7000 Sequence Detection System instrument and data analysis was done with the ABI PRISM 7000 SDS software (Applied Biosystems). 18S RNA was used as the reference housekeeping gene. Specific oligonucleotides pairs were designed by the Applied Biosystems service. Calculations were done as described for the Comparative Method in the User Bulletin 2 of ABI PRISM sequence detection system. A detailed description of the above method can be found in "Penza M et al., Genistein affects adipose tissue deposition in a dose-dependent and gender-specific manner; Endocrinology; 2006 December; 147(12):5740-51 2006"

Figure 7A:
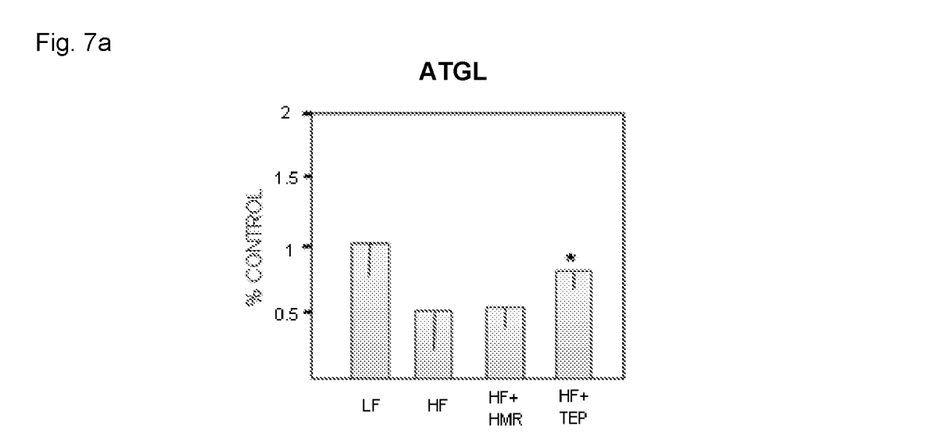
FIGS. 7a, 7b and 7c show the expression of ATGL, PLA2g7 and LPL mRNA in the epidydimal adipose tissue for each mice group measured according to test 8.
Figure 7B:
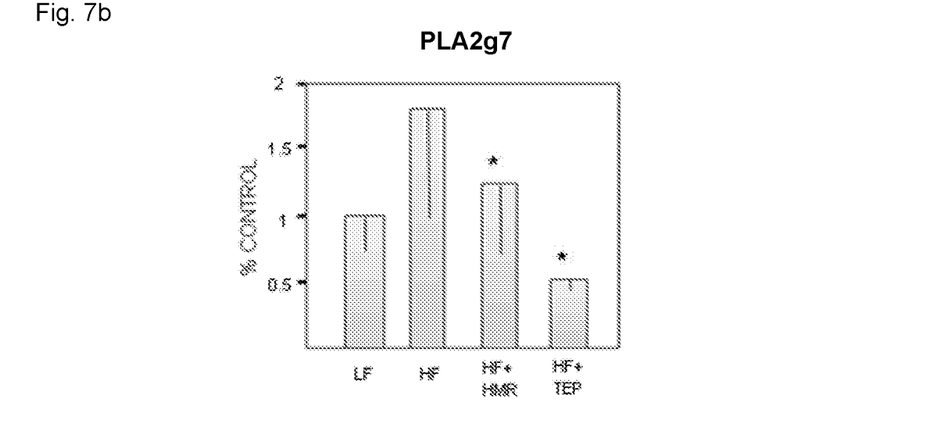
Figure 7C:
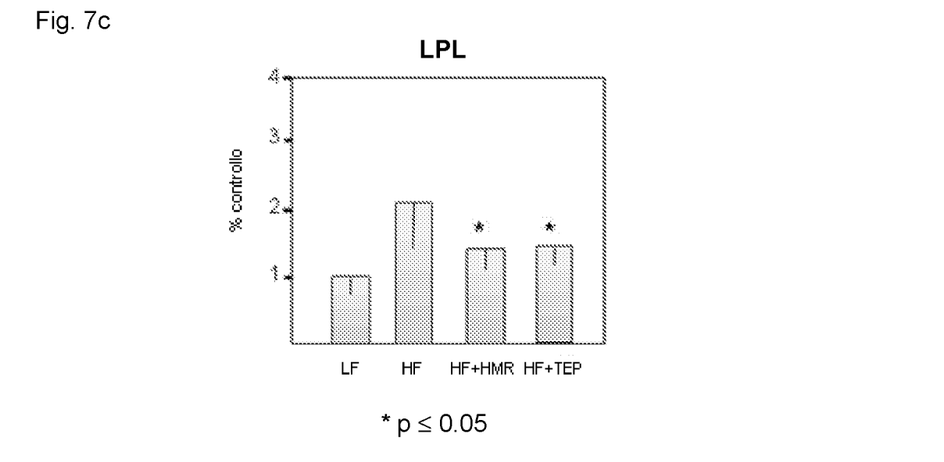

The results were illustrated in FIGS. 7a, 7b, and 7c.

Test 9—Regulation of Genes of the Lipid Metabolism (Liver)

PPARg, belonging to the nuclear receptor superfamily, is essential for adipogenesis. Previous studies suggests that PPARg may have a pivotal role in adipocyte hypertrophy, obesity and insulin resistance. A reduced transcription of the PPARg gene is associated with a decrease of the body mass index (BMI), reduced insulin levels, increased HDL and increased sensitivity to insulin, lowering the risk of type 2 diabetes.

TFEB is a key player in the metabolic response to starvation. TFEB activity is regulated by nutrients. The absence of TFEB results in an impairment of lipid catabolism and in a severe metabolic imbalance in obese animals, whereas TFEB overexpression causes the opposite effects and rescues obesity and associated metabolic syndrome.

The expression of PPARg and TFEB mRNA was measured in the liver of the four groups of mice according to standard procedures as follows.

Total RNA was extracted from 10 to 30 mg of tissue using the RNeasy Lipid Tissue Kit (Qiagen, Maryland, USA) and following the manufacture's instruction. RNA for each sample was reversed transcribed using high capacity cDNA Archive Kit (Applied Biosystems, Foster City, Calif.). Quantitative PCR was performed using Assay on Demand kits based on TaqMan chemistry (Applied Biosystems). RT-PCR reactions were performed on an ABI PRISM 7000 Sequence Detection System instrument and data analysis was done with the ABI PRISM 7000 SDS software (Applied Biosystems). 18S RNA was used as the reference housekeeping gene. Specific oligonucleotides pairs were designed by the Applied Biosystems service. Calculations were done as described for the Comparative Method in the User Bulletin 2 of ABI PRISM sequence detection system. A detailed description of the above method can be found in "Penza M et al., *Genistein affects adipose tissue deposition in a dose-dependent and gender-specific manner; Endocrinology;* 2006 December; 147(12):5740-51 2006"

Figure 8A:
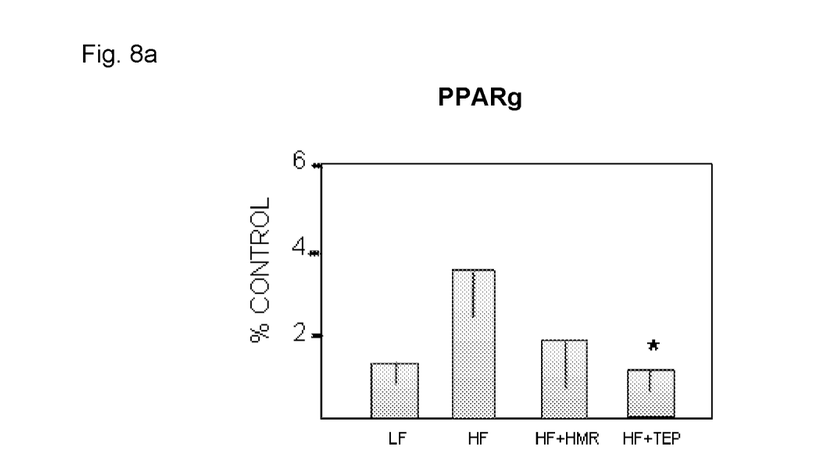
FIGS. 8a and 8b show the expression of PPARg and TFEB mRNA in the liver for each mice group measured according to test 9.
Figure 8B:
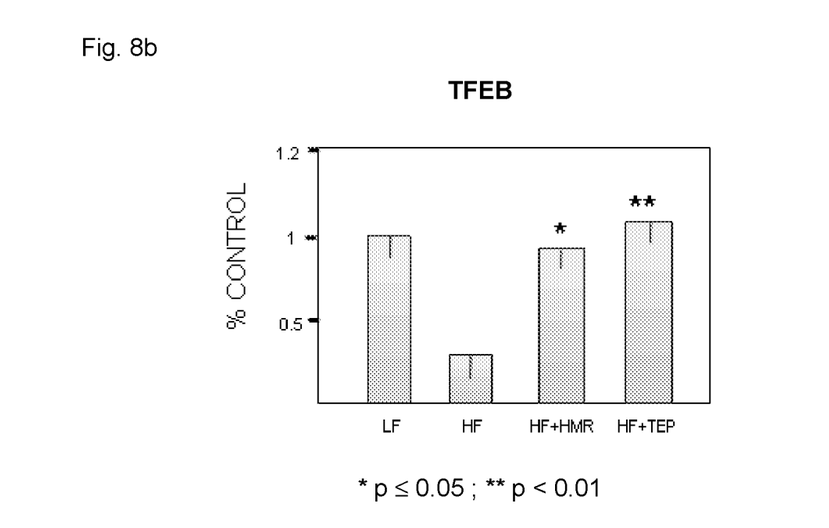

The results were illustrated in FIGS. 8a, and 8b.

Test 10—Oxidative Stress

A. Expression of the Hepatic Antioxidant Enzymes

Glutathione S-transferases (GSTs) comprise a family of eukaryotic and prokaryotic phase II metabolic enzymes best known for their ability to catalyze the conjugation of the reduced form of glutathione (GSH) to xenobiotic substrates for the purpose of detoxification. GSTs can constitute up to 10% of cytosolic protein in some mammalian organs. This activity detoxifies endogenous compounds such as peroxidised lipids and enables the breakdown of xenobiotics. GSTs may also bind toxins and function as transport protein.

The expression of GSTs mRNA was measured in the four groups of mice according to standard procedures as follows.

Total RNA was extracted from 10 to 30 mg of tissue using the RNeasy Lipid Tissue Kit (Qiagen, Maryland, USA) and following the manufacture's instruction. RNA for each sample was reversed transcribed using high capacity cDNA Archive Kit (Applied Biosystems, Foster City, Calif.). Quantitative PCR was performed using Assay on Demand kits based on TaqMan chemistry (Applied Biosystems). RT-PCR reactions were performed on an ABI PRISM 7000 Sequence Detection System instrument and data analysis was done with the ABI PRISM 7000 SDS software (Applied Biosystems). 18S RNA was used as the reference housekeeping gene. Specific oligonucleotides pairs were designed by the Applied Biosystems service. Calculations were done as described for the Comparative Method in the User Bulletin 2 of ABI PRISM sequence detection system. A detailed description of the above method can be found in "Penza M et al., *Genistein affects adipose tissue deposition in a dose-dependent and gender-specific manner; Endocrinology;* 2006 December; 147(12):5740-51 2006"

Figure 9:
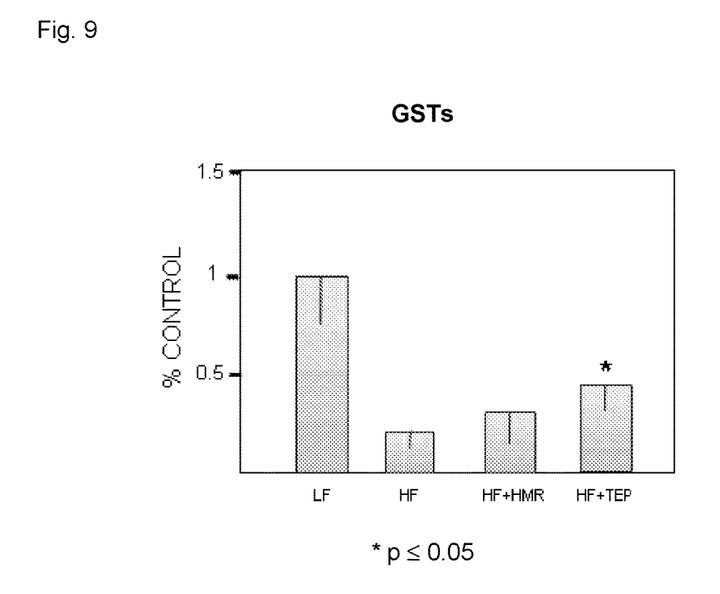
FIG. 9 shows the expression of GSTs mRNA for each mice group measured according to test 10A.

The results were illustrated in FIG. 9.

B. Quantification of Oxidized DNA

8-Hydroxydeoxyguanosine (8OHdG) is the commonly used marker of oxidative stress-derived DNA damage. 8OHdG formation is regulated by local antioxidant capacity and DNA repair enzyme activity. Accordingly, oxidative DNA damage can be assessed from the serum level of the DNA-repair product 8-hydroxydeoxyguanosine (8OHdG), and in particular from the ratio between 8OHdG and its non-oxidized corresponding base 2'-deoxy-guanosine (dGU).

The expression of 8OHdG and dGU mRNA was measured in the four groups of mice according to standard procedures as follows.

DNA Extraction and Digestion.

Genomic DNA was isolated with commercial kit PURE-GENE (Gentra Systems MN, USA), following the manufacturer's instructions, and then quantified using Nanodrop spectrophotometer (Thermo Scientific, DE, USA). 3 µg of DNA for each sample were digested by commercial reagent DNA Degradase Plus (Zymoresearch, CA, USA), a nuclease mixes that degrade DNA to its individual nucleoside components.

LC-MS/MS Reagents.

8-Oxo-7,8-dihydro-2'-deoxyguanosine (8OHdG, ≥98%), 2'-deoxy-guanosine (dGU, ≥8%), 2'-deoxycytidine (dCyt, ≥99%), cotinine-$d_3$ (98%), ascorbic acid, potassium phosphate monobasic, ammonium hydroxide, formic acid, hydrogen peroxide, HPLC-grade water and methanol were purchased from Sigma-Aldrich (Milan, Italy). 5-Methyl-2'-deoxycytidine (5-MedCyt, 98%) and 5-methyl-2'-deoxycytidine-$d_3$ (5-MedCyt-$d_3$) were from TRC (Ontario, Canada). [$^{15}N_5$]dGU (U-$^{15}N_5$, 96-98%) was obtained from Cambridge Isotope Laboratories, INC. (Andover, Mass.). [$^{15}N_5$] 8OHdG had been synthesized from [$^{15}N_5$]dGU according to Hu et al. [Hu, C. W.; Wu, M. T.; Chao, M. R.; Pan, C. H.; Wang, C. J.; Swenberg, J. A.; Wu, K. Y. Comparison of analyses of urinary 8-hydroxy-2'-deoxyguanosine by isotope-dilution liquid chromatography with electrospray tandem mass spectrometry and by enzyme-linked immunosorbent assay, *Rapid Commun. Mass Spectrom.* 18:505-510; 2004] with minor modifications, as described in [Andreoli, R.; Manini, P.; De Palma, G.; Alinovi, R.; Goldoni, M.; Niessen, W. M. A.; Mutti, A. Quantitative determination of urinary 8-oxo-7,8-dihydro-2'-deoxyguanosine, 8-oxo-7,8-dihydroguanine, 8-oxo-7,8-dihydroguano-sine, and their non-oxidized forms: daily concentration profile in healthy volunteers. *Biomarkers* 15:221-231; 2010.]. Stable isotope-labeled compounds were used as internal standards (ISs). All standards were used without further purification.

Sample Collection and Analysis.

After digestion, samples were diluted six times and ultrafiltered with Amicon Ultra 0.5 ml 3K at 13 rpm for 15 minutes. Biomarkers of nucleic acid oxidation and methylation and their unmodified nucleosides, 8OHdG, 5-MedCyt, dGU and dCyt, were performed by isotopic dilution liquid chromatography tandem mass spectrometry (LC-MS/MS) using an API 4000 triple quadrupole mass spectrometer (AB SCIEX, MA, USA) equipped with a TurbolonSpray™ interface for pneumatically assisted electrospray according to the method by Andreoli et al. [cited above], with some modifications to determine SMedCyt and dCyt in the same chromatographic run. Briefly, filtered samples (30 µL) were added with 90 µL of IS aqueous mixture containing 50 nmol/L of [$^{15}N_5$]8OHdG, 5 µmol/L of [$^{15}N_5$]dGU and 600 nmol/L of 5-MedCyt-d$_3$. Then, 10 μL of samples were injected in the chromatographic system. Separation of analytes was performed on an Atlantis®dC$_{18}$ column (100×2.0 mm i.d., 3 μm; Waters, Milford, Mass.) using variable proportions of 10 mmol/l aqueous formic acid (pH 3.75) and methanol at a flow-rate of 0.2 mL/min. Analytes (and ISs) were ionized in positive ion mode and the following SRM transitions were monitored: m/z 284→168 and m/z 289→173 for 8OHdG and its IS [$^{15}$N$_5$]8OHdG; m/z 268→152 and m/z 273→157 for dGU and its IS [$^{15}$N$_5$]dGU; m/z 242→126 and m/z 245→129 for 5-MedCyt and its IS 5-MedCyt-d$_3$; m/z 228→112 for dCyt. For quantitative analysis, working calibrations were obtained by spiking pooled digested samples with standard solutions in the concentrations ranges 0-80 nmol/L for 8OHdG, 0-500 nmol/L for 5-MedCyt, and 0-10 μmol/L for dGU and dCyt. For each analyte, calibration curves were constructed by linear regression analysis of the analyte to IS area ratio versus the known concentration of analytes injected (r$^2$>0.998). For dCyt, 5-MedCyt-d$_3$ was used as internal standard. The LOQ was 0.75 nmol/L for 8OHdG and 5-MedCyt, 1 nmol/L for dGU and dCyt, respectively. The % CV ranged between 2.0% and 6.3% for all analytes and for all intra- and inter-day determinations.

Figure 10:
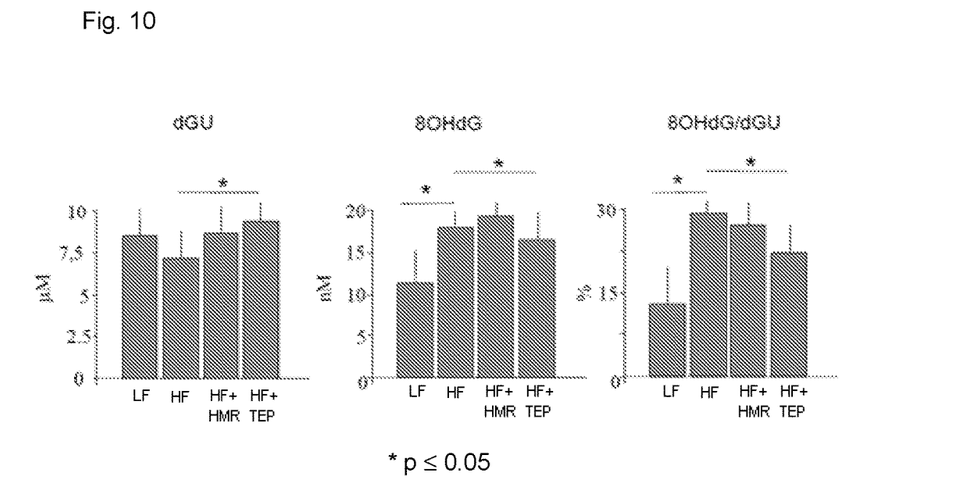
FIG. 10 shows the expression of 8OHdG and dGU mRNA for each mice group measured according to test 10B.

The results were illustrated in FIG. 10.

Test 11—Iron Metabolism

Iron metabolism includes a number of biological reactions maintaining constant the iron level in a human. The control of iron (potentially toxic at higher concentrations) is essential to maintain human health. Iron is essential for red blood cells, where most of the human body's iron is contained. Iron metabolism disorders include iron overload, like hemochromatosis, and iron deficiency, like iron deficiency anemia.

Hepcidin is produced by the liver and appears to be the master regulator of iron homeostasis. Hepcidin regulates (inhibits) iron transport across the intestinal mucosa, thereby preventing excess iron absorption and maintaining normal iron levels within the body. Hepcidin also inhibits transport of iron out of macrophages (site of iron storage and transport). Thus, in states of high hepcidin levels (including inflammatory states), serum iron levels can drop because iron is trapped inside macrophages. Hepcidin has also found to have anti-inflammatory properties in the murine model which acts as a negative feedback in damping inflammation which can cause raised levels.

Ferritin is a ubiquitous intracellular protein that stores iron and releases it in a controlled fashion. The amount of ferritin stored reflects the amount of iron stored. The protein is produced by almost all living organisms, including algae, bacteria, higher plants, and animals. In humans, it acts as a buffer against iron deficiency and iron overload.

Ferroportin is a transmembrane protein that transports iron from the inside of a cell to the outside of it. It is expressed in the liver and enterocytes in the duodenum.

The levels of hepcidin, ferritin and ferroportin are altered in obese people, and obesity is associated with iron depletion.

The levels of hepcidin, ferritin and ferroportin were measured in the four groups of mice according to standard procedures as described, for example, in An-Sheng Zhang et al. "*Suppression of hepatic hepcidin expression in response to acute iron deprivation is associated with an increase of matriptase-2 protein*", Blood. Feb. 3, 2011; 117(5):1687-1699).

Figure 11A:
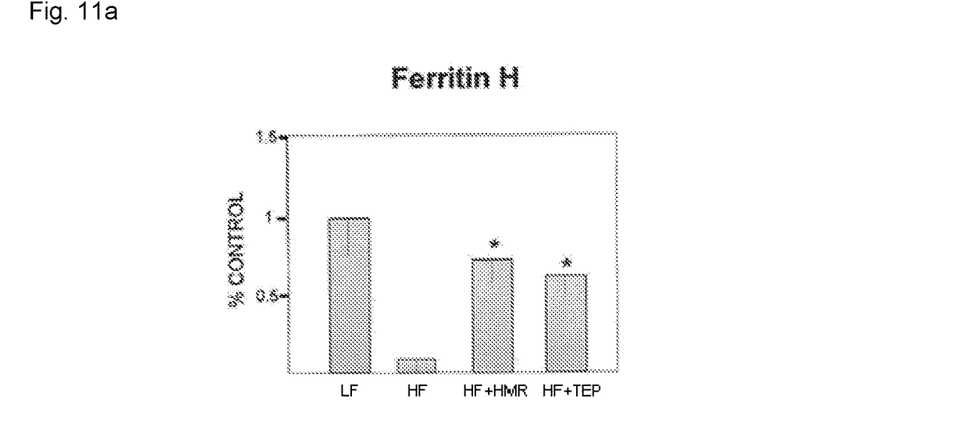
FIGS. 11a, 11b and 11c show the levels of ferritin, ferroportin, and hepcidin, respectively for each mice group measured according to test 11.
Figure 11B:
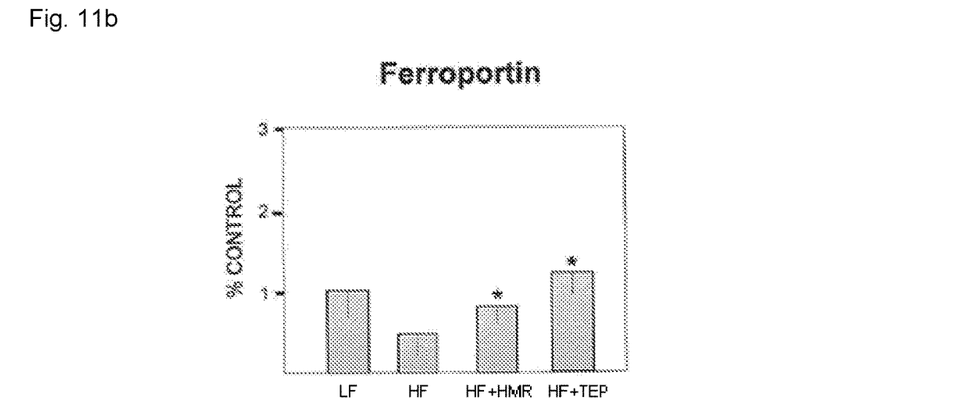
Figure 11C:
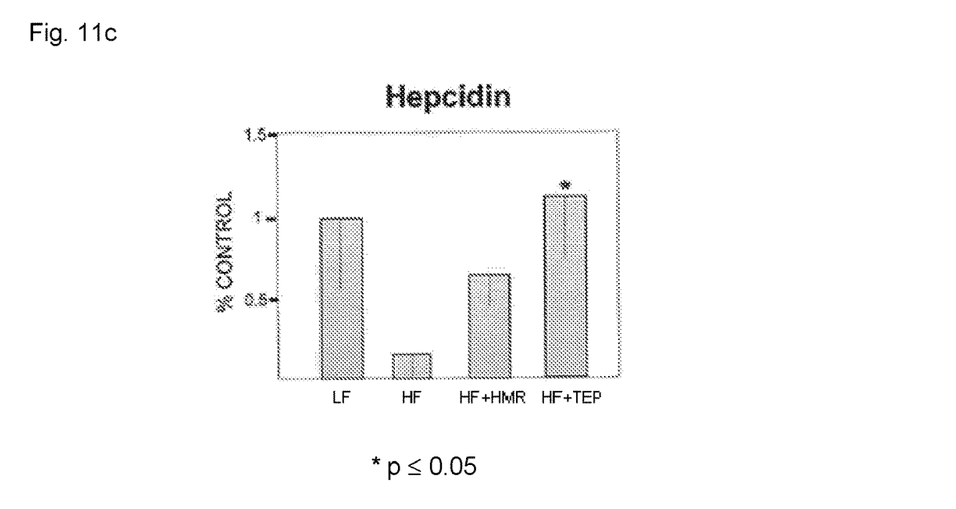

The results were illustrated in FIG. 11.

The invention claimed is:

1. A method for reducing glucose concentration in blood of a person in need thereof, for reducing cholesterol concentration in blood of a person in need thereof, or for reducing a concentration of a pro-inflammatory cytokine in adipose tissue or liver tissue of a person in need thereof, the method comprising:
   administering an effective amount of 7-hydroxymatairesinol (HMR) to the person in need thereof,
   wherein said effective amount is from about 30 to about 300 mg per day.

2. A method for reducing glucose concentration in blood, comprising:
   administering an effective amount of 7-hydroxymatairesinol (HMR) to a person in need thereof,
   wherein said effective amount is from about 30 to about 300 mg per day.

3. The method according to claim 2, wherein said 7-hydroxymatairesinol (HMR) is administered in the form of a pharmaceutical composition, said pharmaceutical composition comprising 7-hydroxymatairesinol (HMR) and at least one pharmaceutically acceptable ingredient and/or excipient.

4. A method according to claim 3, wherein said at least one pharmaceutically acceptable ingredient and/or excipient is an antioxidant.

5. A method according to claim 2, wherein said 7-hydroxymatairesinol (HMR) is administered in the form of a food product, said food product comprising 7-hydroxymatairesinol (HMR) and at least one edible ingredient and/or excipient.

6. A method according to claim 5, wherein said at least one pharmaceutically acceptable ingredient and/or excipient is an antioxidant.

7. A method for reducing cholesterol concentration in blood, comprising:
   administering an effective amount of 7-hydroxymatairesinol (HMR) to a person in need thereof,
   wherein said effective amount is from about 30 to about 300 mg per day.

8. A method according to claim 7, wherein said 7-hydroxymatairesinol (HMR) is administered in the form of a pharmaceutical composition, said pharmaceutical composition comprising 7-hydroxymatairesinol (HMR) and at least one pharmaceutically acceptable ingredient and/or excipient.

9. A method according to claim 8, wherein said at least one pharmaceutically acceptable ingredient and/or excipient is an antioxidant.

10. A method according to claim 7, wherein said 7-hydroxymatairesinol (HMR) is administered in the form of a food product, said food product comprising 7-hydroxymatairesinol (HMR) and at least one edible ingredient and/or excipient.

11. A method according to claim 10, wherein said at least one pharmaceutically acceptable ingredient and/or excipient is an antioxidant.

12. A method for reducing a concentration of a pro-inflammatory cytokine in adipose tissue or liver tissue, comprising:
   administering an effective amount of 7-hydroxymatairesinol (HMR) to a person in need thereof,
   wherein said effective amount is from about 30 to about 300 mg per day.

13. A method according to claim 12, wherein said 7-hydroxymatairesinol (HMR) is administered in the form of a pharmaceutical composition, said pharmaceutical composition comprising 7-hydroxymatairesinol (HMR) and at least one pharmaceutically acceptable ingredient and/or excipient.

14. A method according to claim 13, wherein said at least one pharmaceutically acceptable ingredient and/or excipient is an antioxidant.

15. A method according to claim 12, wherein said 7-hydroxymatairesinol (HMR) is administered in the form of a food product, said food product comprising 7-hydroxymatairesinol (HMR) and at least one edible ingredient and or excipient.

16. A method according to claim 15, wherein said at least one pharmaceutically acceptable ingredient and/or excipient is an antioxidant.

\* \* \* \* \*